United States Patent [19]

Teng et al.

[11] Patent Number: 5,688,957

[45] Date of Patent: Nov. 18, 1997

[54] [(3"-THIOXACYCLOHEX-1"-ENYL)]-BUT-3'-ENE-1'-YNYL]ARYL AND [(3"-THIOXACYCLOHEX-1"-ENYL)]-BUT-3'-ENE-1'-YNYL]HETEROARYL CARBOXYLIC ACIDS AND ESTERS HAVING RETINOID-LIKE BIOLOGICAL ACTIVITY

[75] Inventors: Min Teng, Aliso Viejo; Roshantha A. Chandraratna, Mission Viejo, both of Calif.

[73] Assignee: Allergan, Waco, Tex.

[21] Appl. No.: 581,121

[22] Filed: Dec. 29, 1995

[51] Int. Cl.$^6$ .................. C07D 335/02; C07D 409/10
[52] U.S. Cl. .................. 546/280.1; 544/238; 544/333; 548/146; 548/190; 548/215; 548/233; 549/13; 549/28
[58] Field of Search .................. 544/238, 333; 546/280.1; 548/146, 190, 215, 233; 549/13, 28

[56] References Cited

U.S. PATENT DOCUMENTS

| | | |
|---|---|---|
| 4,096,341 | 6/1978 | Frazer . |
| 4,326,055 | 4/1982 | Loeliger . |
| 4,391,731 | 7/1983 | Boller et al. .................. 252/299.62 |
| 4,695,649 | 9/1987 | Magami et al. . |
| 4,723,028 | 2/1988 | Shudo . |
| 4,739,098 | 4/1988 | Chandraratna . |
| 4,740,519 | 4/1988 | Shroot et al. . |
| 4,810,804 | 3/1989 | Chandraratna . |
| 4,826,969 | 5/1989 | Maignan et al. . |
| 4,826,984 | 5/1989 | Berlin et al. .................. 546/134 |

(List continued on next page.)

FOREIGN PATENT DOCUMENTS

| | | | |
|---|---|---|---|
| 0098591 | 1/1984 | European Pat. Off. | ....... C07D 333/54 |
| 0130795 | 1/1985 | European Pat. Off. | ....... C07D 311/58 |
| 170105A | 2/1986 | European Pat. Off. | . |
| 0176032 | 4/1986 | European Pat. Off. | ......... C07C 65/38 |
| 0176033 | 4/1986 | European Pat. Off. | ....... C07D 261/18 |
| 176034A | 4/1986 | European Pat. Off. | ......... C07C 63/66 |
| 0253302 | 1/1988 | European Pat. Off. | ....... C07D 213/16 |
| 0272921 | 6/1988 | European Pat. Off. | ....... C07D 213/80 |
| 272921 | 6/1988 | European Pat. Off. | . |
| 0284288 | 9/1988 | European Pat. Off. | ....... C07D 401/04 |
| 0303915 | 2/1989 | European Pat. Off. | ..... A61K 31/255 |
| 0315071 | 5/1989 | European Pat. Off. | ......... C07C 63/66 |
| 0350846 | 7/1989 | European Pat. Off. | ....... C07D 311/58 |
| 0661259 | 5/1995 | European Pat. Off. | ....... C07C 233/81 |
| 3316932 | 11/1983 | Germany | .................. C07C 63/66 |
| 3524199 | 1/1986 | Germany | .................. C07C 63/66 |
| 3602473 | 7/1987 | Germany | .................. C07C 43/215 |
| 3708060 | 9/1987 | Germany | .................. C07D 311/04 |
| 3715955 | 11/1987 | Germany | .................. C07C 15/58 |
| 2190378 | 11/1987 | United Kingdom | ............ C07C 39/21 |
| 8500806 | 2/1985 | WIPO | .................. A61K 31/00 |
| 8504652 | 10/1985 | WIPO | .................. A61K 31/19 |
| WO9116051 | 10/1991 | WIPO | .................. A61K 31/44 |
| WO9206948 | 4/1992 | WIPO | .................. C07C 69/86 |

OTHER PUBLICATIONS

Dawson et al., Chemistry and Biology of Synthetic Retinoids, pp. 307–356, 1990.

A General Synthesis of Terminal and Internal Arylalkynes by the Palladium–Catalyzed Reaction of Alkynylzinc Reagents with Aryl Halides by Anthony O. King and Ei–ichi Negishi, *J. Org. Chem.* 43 No. 2, 1978 p. 358.

Conversion of Methyl Ketones into Terminal Acetylenes and (E)–Tri–substituted Olefins of Terpenoid Origin by Ei–ichi, Anthony O. King, and William L. Klima, *J. Org. Chem.* 45 No. 12, 1980 p. 2526.

Sporn et. al. in *J. Amer. Acad. Derm.* 15:756–764 (1986).

A Convenient Synthesis of Ethynylarenes and Diethynylarenes by S. Takahashi, Y. Kuroyama, K. Sonogashira, N. Hagihara, *Synthesis* 1980 pp. 627–630.

Shudo et al. in *Chem. Phar. Bull.* 33:404–407 (1985).

Kagechika et. al. in *J. Med. Chem.* 31:2182–2192 (1988).

(List continued on next page.)

*Primary Examiner*—C. Warren Ivy
*Assistant Examiner*—Lyman H. Smith
*Attorney, Agent, or Firm*—Gabor L. Szekeres; Robert J. Baran; Martin A. Voet

[57] ABSTRACT

Compounds of the formula

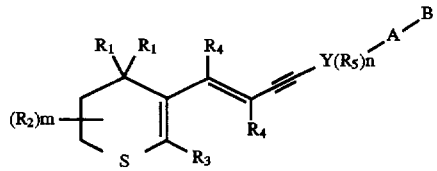

where $R_1$, $R_2$, $R_3$, and $R_4$ independently are H or lower alkyl of 1 to 10 carbons; $R_5$ is lower alkyl of 1 to 10 carbons, fluoro, chloro, bromo, iodo, nitro, or fluoroalkyl having 1 to 10 carbons; m is an integer having the value of 1–4; n is an integer having the value of 0–4; Y is phenyl or a heteroaryl group selected from a group consisting of pyridyl, thienyl, furyl, pyridazinyl, pyrimidinyl, pyrazinyl, thiazolyl and oxazolyl, said Y group being optionally substituted with one or more $R_5$ group; A is $(CH_2)_p$ where p is 0–5, lower branched chain alkyl having 3–6 carbons, cycloalkyl having 3–6 carbons, alkenyl having 2–6 carbons and 1 or 2 double bonds, alkynyl having 2–6 carbons and 1 or 2 triple bonds, and B is hydrogen, COOH or a pharmaceutically acceptable salt thereof, $COOR_8$, $CONR_9R_{10}$, $—CH_2OH$, $CH_2OR_{11}$, $CH_2OCOR_{11}$, CHO, $CH(OR_{12})_2$, $CHOR_{13}O$, $—COR_7$, $CR_7(OR_{12})_2$, or $CR_7OR_{13}O$, where $R_7$ is an alkyl, cycloalkyl or alkenyl group containing 1 to 5 carbons, $R_8$ is an alkyl group of 1 to 10 carbons, or a cycloalkyl group of 5 to 10 carbons, or $R_8$ is phenyl or lower alkylphenyl, $R_9$ and $R_{10}$ independently are hydrogen, an alkyl group of 1 to 10 carbons, or a cycloalkyl group of 5–10 carbons, or phenyl or lower alkylphenyl, $R_{11}$ is lower alkyl, phenyl or lower alkylphenyl, $R_{12}$ is lower alkyl, and $R_{13}$ is divalent alkyl radical of 2–5 carbons have retinoid-like biological activity.

22 Claims, No Drawings

U.S. PATENT DOCUMENTS

| | | |
|---|---|---|
| 4,855,320 | 8/1989 | Chatterjee et al. |
| 4,895,868 | 1/1990 | Chandraratna. |
| 4,927,947 | 5/1990 | Chandraratna ............................ 549/484 |
| 4,980,369 | 12/1990 | Chandraratna. |
| 4,992,468 | 2/1991 | Chandraratna. |
| 5,005,550 | 4/1991 | Chandraratna. |
| 5,013,744 | 5/1991 | Chandraratna. |
| 5,015,658 | 5/1991 | Chandraratna. |
| 5,023,341 | 6/1991 | Chandraratna. |
| 5,037,825 | 8/1991 | Klaus et al. ............................ 514/233.8 |
| 5,045,551 | 9/1991 | Chandraratna. |
| 5,053,523 | 10/1991 | Chandraratna. |
| 5,068,252 | 11/1991 | Chandraratna. |
| 5,089,509 | 2/1992 | Chandraratna. |
| 5,130,335 | 7/1992 | Chandraratna. |
| 5,134,159 | 7/1992 | Chandraratna. |
| 5,162,546 | 11/1992 | Chandraratna ............................ 549/23 |
| 5,175,185 | 12/1992 | Chandraratna ............................ 514/445 |
| 5,183,827 | 2/1993 | Chandraratna ............................ 514/444 |
| 5,202,471 | 4/1993 | Chandraratna ............................ 562/473 |
| 5,231,113 | 7/1993 | Chandraratna ............................ 514/510 |
| 5,234,926 | 8/1993 | Chandraratna ............................ 514/253 |
| 5,248,777 | 9/1993 | Chandraratna ............................ 546/165 |
| 5,256,694 | 10/1993 | Wuest et al. ............................ 514/549 |
| 5,264,456 | 11/1993 | Chandraratna ............................ 514/461 |
| 5,264,578 | 11/1993 | Chandraratna ............................ 546/269 |
| 5,272,156 | 12/1993 | Chandraratna ............................ 514/314 |
| 5,278,318 | 1/1994 | Chandraratna ............................ 549/23 |
| 5,324,744 | 6/1994 | Chandraratna ............................ 514/456 |
| 5,324,840 | 6/1994 | Chandraratna ............................ 546/318 |
| 5,326,898 | 7/1994 | Chandraratna ............................ 560/17 |
| 5,344,959 | 9/1994 | Chandraratna ............................ 560/100 |
| 5,346,895 | 9/1994 | Chandraratna ............................ 514/247 |
| 5,346,915 | 9/1994 | Chandraratna ............................ 514/432 |
| 5,348,972 | 9/1994 | Chandraratna ............................ 514/432 |
| 5,348,975 | 9/1994 | Chandraratna ............................ 514/456 |
| 5,349,105 | 9/1994 | Chandraratna ............................ 564/163 |
| 5,354,752 | 10/1994 | Chandraratna ............................ 514/252 |
| 5,380,877 | 1/1995 | Chandraratna ............................ 549/60 |
| 5,391,753 | 2/1995 | Chandraratna ............................ 546/63 |
| 5,399,561 | 3/1995 | Chandraratna ............................ 514/252 |
| 5,399,586 | 3/1995 | Davies et al. ............................ 514/448 |
| 5,407,937 | 4/1995 | Chandraratna ............................ 514/256 |
| 5,414,007 | 5/1995 | Chandraratna ............................ 514/365 |
| 5,426,118 | 6/1995 | Chandraratna ............................ 514/337 |
| 5,434,173 | 7/1995 | Chandraratna ............................ 514/354 |
| 5,451,605 | 9/1995 | Chandraratna et al. ............................ 514/475 |
| 5,455,265 | 10/1995 | Chandraratna ............................ 514/448 |
| 5,468,879 | 11/1995 | Chandraratna ............................ 549/23 |
| 5,470,999 | 11/1995 | Chandraratna ............................ 560/100 |
| 5,475,022 | 12/1995 | Chandraratna ............................ 514/448 |
| 5,475,113 | 12/1995 | Chandraratna ............................ 548/203 |
| 5,489,584 | 2/1996 | Vuligonda et al. ............................ 514/188 |
| 5,498,755 | 3/1996 | Chandraratna et al. ............................ 562/272 |
| 5,498,795 | 3/1996 | Song et al. ............................ 562/474 |
| 5,543,534 | 8/1996 | Vuligonda et al. ............................ 549/421 |

OTHER PUBLICATIONS

Chemistry and Biology of Synthetic Retinoids by Marcia L. Dawson and William H. Okamura, published by CRC Press Inc., 1990, p. 334–335, 354.

Synthesis of 2,2'–Diacyl–1,1'–biaryls. Regiocontrolled Protection of . . . by Mervic, et al, *J. Org. Chem.*, No. 45, pp. 4720–4725, 1980.

A Dopamine Receptor Model and Its Application in the Design of a New Class of Rigid Pyrrolo[2,3–g]isoquinoline Antipsychotics, Gary L. Olson, et al. *American Chemical Society*, 1981, vol. 24, No. 9, pp. 1026–1031.

6.2.3. Conformational Restriction, Williams, et al., *Drug Discovery and Development*, 1987 The Humana Press, pp. 54–55.

V. Retinoid Structure–Biological Activity Relationships, Chemistry and Biology of Synthetic Retinoids, pp. 324–356, 1990.

Synthesis of 6–substituted–3,4–dihydro–2 H–1–benzopyran–2–ones (dihydrocoumarihs) Via pelladium catalyzed coupling reactions, Davis et al. *J. Organomettalic Chem* 387 (1990) 381–390.

Effects of 13–Cis–Retinoic Acid, All–Trans–Retinoic Acid, and Acitretin on the Proliferation, Lipid Synthesis and Keratin Expression of Cultured Human Sebocytes In Vitro, C. C. Zouboulis, *The Journal of Investigative Dermatology*, vol. 96, No. 5, May 1991, pp. 792–797.

Organ maintenance of human sebaceous glands: in vitro effects of 13–cis retinoic acid and testosterone, John Ridden, et al., *Journal of Cell Science*, vol. 95, 1990, pp. 125–136.

Characterization of Human Sebaceous Cells In Vitro, Thomas I. Doran, et al., *The Journal of Investigative Dermatology*, vol. 96, No. 3, Mar. 1991.

Synthesis and Evaulation of Stilbene and Dihydrostilbene Derivatives as Potential Anticancer Agents That Inhibit Tubulin Polymerization by Cushman, Mark et.al. *J. Med. Chem* 1991, 34, 2579–2588.

Synthesis and Evaluation of New Protein–Tyrosine Kinase Inhibitors. Part 1. Pyridine–Containing Stilbenes and Amides by Cushman, Mark et al. *Biorganic & Medicinal Chemistry Letters*, vol. 1, No. 4, pp. 211–214, 1991.

Di–and Tri–methoxystyryl Derivatives of Reterocyclic Nitrogen Compounds by Bahner, C.T. et al. Arzneim–Forsch./Drug Res, 31 (I), Nr. 3 (1981).

Retinobenzoic acids. 3. Structure–Activity Relationships of retinoidal Azobenzene–4–carboxylic acids and Stilbene–4–carboxylic acids by H. Kagechika et al., *Journal of Medicinal Chemistry*, 1989, 32 pp. 1098–1108.

[(3"-THIOXACYCLOHEX-1"-ENYL)]-BUT-3'-ENE-1'-YNYL]ARYL AND [(3"-THIOXACYCLOHEX-1"-ENYL)]-BUT-3'-ENE-1'-YNYL]HETEROARYL CARBOXYLIC ACIDS AND ESTERS HAVING RETINOID-LIKE BIOLOGICAL ACTIVITY

BACKGROUND OF THE INVENTION

1. Field of the Invention

The present invention is directed to novel compounds which have retinoid-like biological activity. More specifically, the present invention relates to [(3"-thioxacyclohexyl"-enyl)]-but-3'-ene-1'-ynyl]aryl and [(3"-thioxacyclohex-1"-enyl)]-but-3'-ene-1'-ynyl]heteroaryl carboxylic acid and ester derivatives. The acid or ester function, may also be converted to an alcohol, aldehyde or ketone, or derivatives thereof, or may be reduced to —$CH_3$.

2. Related Art

Compounds which have retinoid like activity are well known in the art, and are described in numerous United States and foreign patents and in scientific publications. It is generally known and accepted in the art that retinoid like activity is useful for treating animals of the mammalian species, including humans, for curing or alleviating the symptoms and conditions of numerous diseases and conditions. In other words, it is generally accepted in the art that pharmaceutical compositions having a retinoid-like compound or compounds as the active ingredient are useful as regulators of cell proliferation and differentiation, and particularly as agents for treating skin-related diseases, including, actinic keratoses, arsenic keratoses, inflammatory and non-inflammatory acne, psoriasis, ichthyoses and other keratinization and hyperproliferative disorders of the skin, eczema, atopic dermatitis, Darriers disease, lichen planus, prevention and reversal of glucocorticoid damage (steroid atrophy), as a topical anti-microbial, as skin antipigmentation agents and to treat and reverse the effects of age and photo damage to the skin. Retinoid compounds are also useful for the prevention and treatment of cancerous and precancerous conditions, including, premalignant and malignant hyperproliferative diseases such as cancers of the breast, skin, prostate, cervix, uterus, colon, bladder, esophagus, stomach, lung, larynx, oral cavity, blood and lymphatic system, metaplasias, dysplasias, neoplasias, leukoplakias and papillomas of the mucous membranes and in the treatment of Kaposi's sarcoma. In addition, retinoid compounds can be used as agents to treat diseases of the eye, including, without limitation, proliferative vitreoretinopathy (PVR), retinal detachment, dry eye and other corneopathies, as well as in the treatment and prevention of various cardiovascular diseases, including, without limitation, diseases associated with lipid metabolism such as dyslipidemias, prevention of post-angioplasty restenosis and as an agent to increase the level of circulating tissue plasminogen activator (TPA). Other uses for retinoid compounds include the prevention and treatment of conditions and diseases associated with human papilloma virus (HPV), including warts and genital warts, various inflammatory diseases such as pulmonary fibrosis, ileitis, colitis and Krohn's disease, neurodegenerative diseases such as Alzheimer's disease, Parkinson's disease and stroke, improper pituitary function, including insufficient production of growth hormone, modulation of apoptosis, including both the induction of apoptosis and inhibition of T-Cell activated apoptosis, restoration of hair growth, including combination therapies with the present compounds and other agents such as Minoxidil®, diseases associated with the immune system, including use of the present compounds as immunosuppressants and immunostimulants, modulation of organ transplant rejection and facilitation of wound healing, including modulation of chelosis.

U.S. Pat. No. 4,810,804 discloses such disubstituted acetylene compounds wherein one of the substituents of the acetylene group is a substituted phenyl group, and the second substituent is substituted or unsubstituted 6-chromanyl, 6-thiochromanyl or 6-tetrahydroquinolinyl group. The compounds disclosed and claimed in U.S. Pat. No. 4,810,804 have retinoid acid-like biological activity.

A published European patent application of the present applicant (Publication No. 0284288, published on Sep. 28, 1988) describes compounds having retinoic acid-like activity which are 4,4-disubsituted 6-chromanyl, 4,4-disubsituted 6-thiochromanyl and 4,4-disubsituted 6-tetrahydroquinolinyl acetylenes also substituted by a substituted heteroaryl group.

U.S. Pat. Nos. 5,013,744, 5,023,341, 5,053,523, and 5,089,509 describe ethyne compounds substituted with a heteroaromatic or monocyclic aromatic substituent and also with a second monocyclic aromatic or heteroaromatic substituent. U.S. Patent No. 5,399,561 describes ethyne compounds which have a phenyl or a heteroaryl substituent and also a 2-oxochromanyl, 2-oxothiochromanyl or 2-oxo-1,2,3,4-tetrahydroquinolinyl substituent.

U.S. Pat. Nos. 4,992,468, 5,068,252, 5,175,185, 5,202,471, 5,264,456, 5,324,840, 5,326,898, 5,349,105, 5,391,753, 5,414,007 and 5,434,173 (assigned to the same assignee as the present application) and patents and publications cited therein, describe or relate to compounds which have retinoid-like biological activity and a structure wherein a phenyl and a heteroaryl or a phenyl and a second phenyl group is linked with an olephinic or acetylenic linkage.

Published European Application 0 272 921 (published on Jun. 29, 1988 describes [(cyclohex-1"-enyl)-but-3'-ene-1'-ynyl]heteroaryl carboxylic acids. Substantially the same disclosure is found in U.S. Pat. No. 4,927,947. U.S. Pat. No. 4,739,098 describes [(cyclohex-1"-enyl)-but-3'-ene-1'-ynyl] benzoic acids, and U.S. Pat. No. 5,426,118 describes [4-(1,2-epoxycyclohaxanyl)but-3-en-1-ynyl)aromatic and heteroaromatic acids.

The compounds described in these patents have retinoid-like biological activity. Numerous further United States patents and applications for patent assigned to the same assignee as the present invention, are directed to compounds having retinoid-like biological activity.

SUMMARY OF INVENTION

The present invention relates to compounds of Formula 1

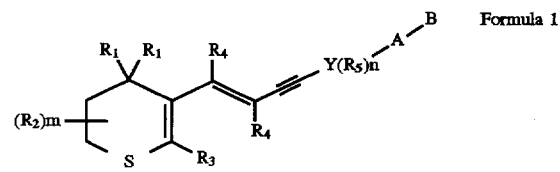

Formula 1 where $R_1$, $R_2$, $R_3$, and $R_4$ independently are H or lower alkyl of 1 to 10 carbons;

$R_5$ is lower alkyl of 1 to 10 carbons, fluoro, chloro, bromo, iodo, nitro, or fluoroalkyl having 1 to 10 carbons;

m is an integer having the value of 1–4;

n is an integer having the value of 0–4;

Y is phenyl or a heteroaryl group selected from a group consisting of pyridyl, thienyl, furyl, pyridazinyl, pyrimidinyl, pyrazinyl, thiazolyl and oxazolyl, said Y group being optionally substituted with one or more $R_5$ group;

A is $(CH_2)_p$ where p is 0–5, lower branched chain alkyl having 3–6 carbons, cycloalkyl having 3–6 carbons, alkenyl having 2–6 carbons and 1 or 2 double bonds, alkynyl having 2–6 carbons and 1 or 2 triple bonds, and B is hydrogen, COOH or a pharmaceutically acceptable salt thereof, $COOR_8$, $CONR_9R_{10}$, —$CH_2OH$, $CH_2OR_{11}$, $CH_2OCOR_{11}$, CHO, $CH(OR_{12})_2$, $CHOR_{13}O$, —$COR_7$, $CR_7(OR_{12})_2$, or $CR_7OR_{13}O$, where $R_7$ is an alkyl, cycloalkyl or alkenyl group containing 1 to 5 carbons, $R_8$ is an alkyl group of 1 to 10 carbons, or a cycloalkyl group of 5 to 10 carbons, or $R_8$ is phenyl or lower alkylphenyl, $R_9$ and $R_{10}$ independently are hydrogen, an alkyl group of 1 to 10 carbons, or a cycloalkyl group of 5–10 carbons, or phenyl or lower alkylphenyl, $R_{11}$ is lower alkyl, phenyl or lower alkylphenyl, $R_{12}$ is lower alkyl, and $R_{13}$ is divalent alkyl radical of 2–5 carbons.

In a second aspect, this invention relates to the use of the compounds of Formula 1 for the treatment of skin-related diseases, including, without limitation, actinic keratoses, arsenic keratoses, inflammatory and non-inflammatory acne, psoriasis, ichthyoses and other keratinization and hyperproliferative disorders of the skin, eczema, atopic dermatitis, Darriers disease, lichen planus, prevention and reversal of glucocorticoid damage (steroid atrophy), as a topical antimicrobial, as skin anti-pigmentation agents and to treat and reverse the effects of age and photo damage to the skin. The compounds are also useful for the prevention and treatment of cancerous and precancerous conditions, including, premalignant and malignant hyperproliferative diseases such as cancers of the breast, skin, prostate, cervix, uterus, colon, bladder, esophagus, stomach, lung, larynx, oral cavity, blood and lymphatic system, metaplasias, dysplasias, neoplasias, leukoplakias and papillomas of the mucous membranes and in the treatment of Kaposi's sarcoma. In addition, the present compounds can be used as agents to treat diseases of the eye, including, without limitation, proliferative vitreoretinopathy (PVR), retinal detachment, dry eye and other corneopathies, as well as in the treatment and prevention of various cardiovascular diseases, including, without limitation, diseases associated with lipid metabolism such as dyslipidemias, prevention of post-angioplasty restenosis and as an agent to increase the level of circulating tissue plasminogen activator (TPA). Other uses for the compounds of the present invention include the prevention and treatment of conditions and diseases associated with human papilloma virus (HPV), including warts and genital warts, various inflammatory diseases such as pulmonary fibrosis, ileitis, colitis and Krohn's disease, neurodegenerative diseases such as Alzheimer's disease, Parkinson's disease and stroke, improper pituitary function, including insufficient production of growth hormone, modulation of apoptosis, including both the induction of apoptosis and inhibition of T-Cell activated apoptosis, restoration of hair growth, including combination therapies with the present compounds and other agents such as Minoxidil®, diseases associated with the immune system, including use of the present compounds as immunosuppressants and immunostimulants, modulation of organ transplant rejection and facilitation of wound healing, including modulation of chelosis.

This invention also relates to a pharmaceutical formulation comprising a compound of Formula 1 in admixture with a pharmaceutically acceptable excipient.

In another aspect, this invention relates to process for making a compound of Formula 1 which process comprises:

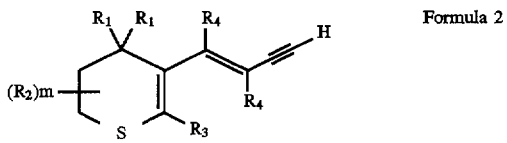

Formula 2

Formula 3

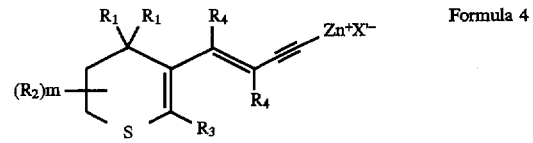

Formula 4 reacting a compound of Formula 2 with a compound of Formula 3 in the presence of cuprous iodide and $Pd(PQ_3)2Cl_2$ (Q is phenyl) or a similar complex, giving the corresponding compound of Formula 1; or to the process of making a compound of Formula 1 which consists of reacting a zinc salt of Formula 4 with a compound of Formula 3 in the presence of $Pd(PQ_3)_4$ (Q is phenyl) or a similar complex. In Formulas 2, 3 and 4 the symbols $R_1$, $R_2$, $R_3$, $R_4$, $R_5$, Y, A, m and n have the same definition as in connection with Formula 1, X is a halogen, preferably I, B is H, or a protected acid, alcohol, aldehyde, or ketone, and $X^-$ is a monovalent anion such as chloride, bromide or iodide.

Still further the present invention relates to the processes of homologating a compound of Formula 1 where A is $(CH_2)_n$ and n is 0–4 to give an acid of Formula 1; or converting an acid of Formula 1 to a salt; or forming an acid addition salt;

converting an acid of Formula 1 to an ester; or converting an acid of Formula 1 to an amide; or reducing an acid of Formula 1 to an alcohol or aldehyde; or converting an alcohol of Formula 1 to an ether or ester; or oxidizing an alcohol of Formula 1 to an aldehyde; or converting an aldehyde of Formula 1 to an acetal; or converting a ketone of Formula 1 to a ketal.

DETAILED DESCRIPTION OF THE INVENTION

General Embodiments

Definitions

The term alkyl refers to and covers any and all groups which are known as normal alkyl, branched-chain alkyl and cycloalkyl. The term alkenyl refers to and covers normal alkenyl, branch chain alkenyl and cycloalkenyl groups having one or more sites of unsaturation. Unless stated otherwise in these specifications lower alkyl means the above-defined broad definition of alkyl groups having 1 to 6 carbons, and as applicable, 3 to 6 carbons for branch chained and cyclo-alkyl groups. Lower alkenyl is defined similarly having 2 to 6 carbons for normal alkenyl, and 3 to 6 carbons for branch chained and cycloalkenyl groups.

The term "ester" as used here refers to and covers any compound falling within the definition of that term as classically used in organic chemistry. It includes organic and inorganic esters. Where B (of Formula 1) is —COOH, this term covers the products derived from treatment of this function with alcohols or thioalcohols preferably with aliphatic alcohols having 1-6 carbons. Where the ester is derived from compounds where B is —CH$_2$OH, this term covers compounds derived from organic acids capable of forming esters including phosphorous based and sulfur based acids, or compounds of the formula —CH$_2$OCOR$_{11}$ where R$_{11}$ is defined as above.

The term "amides" has the meaning classically accorded that term in organic chemistry. In this instance it includes the unsubstituted amides and all aliphatic and aromatic mono- and di- substituted amides.

A pharmaceutically acceptable salt may be prepared for any compounds in this invention having a functionality capable of forming such salt, for example an acid functionality. A pharmaceutically acceptable salt is any salt which retains the activity of the parent compound and does not impart any deleterious or untoward effect on the subject to which it is administered and in the context in which it is administered.

Pharmaceutically acceptable salts may be derived from organic or inorganic bases. The salt may be a mono or polyvalent ion. Of particular interest are the inorganic ions, sodium, potassium, calcium, and magnesium. Organic salts may be made with amines, particularly ammonium salts such as mono-, di- and trialkyl amines or ethanol amines. Salts may also be formed with caffeine, tromethamine and similar molecules. Where there is a nitrogen sufficiently basic as to be capable of forming acid addition salts, such may be formed with any inorganic or organic acids or alkylating agent such as methyl iodide. Preferred salts are those formed with inorganic acids such as hydrochloric acid, sulfuric acid or phosphoric acid. Any of a number of simple organic acids such as mono-, di- or tri- acid may also be used.

The compounds of the present invention contain at least two double bonds, and therefore have trans and cis (E and Z) isomers. However, presently it was found that only the trans isomers of the exocyclic double bond have significant retinoid-like biological activity. In addition, the compounds of the present invention may contain one or more chiral centers and therefore exist in enantiomeric and diastereomeric forms. The scope of the present invention is intended to cover trans isomers, mixtures of cis and trans isomers, mixtures of diastereomers and racemic mixtures of enantiomers (optical isomers) as well.

With reference now to Formula 1, the preferred compounds of this invention are those where Y is phenyl, pyridyl, thienyl or furyl, with the phenyl and pyridyl derivatives being particularly preferred. When Y is phenyl, compounds are preferred where the ethynyl group and the A—B group are attached to the 1 and 4 positions respectively of a benzene ring (i.e., where the phenyl moiety of the compound is para substituted). When the Y group is pyridyl, thienyl or furyl, compounds are preferred where the ethynyl group and the A—B group are attached to the 2 and 5 positions respectively of a pyridine ring (the 6 and 3 positions of the nicotinic acid nomenclature being equivalent to the 2/5 designation in the pyridine nomenclature) or to the 5 and 2 positions respectively of a thiophene or furan group, respectively. Compounds where Y is phenyl, and where the phenyl group is para substituted and compounds where Y is pyridyl and the pyridyl group is 2,5-substituted in the above-described manner, are particularly preferred.

With regard to the A—B side chain (substituent) on the phenyl or heteroaryl group Y, compounds are preferred where A is (CH$_2$)$_p$ and p is 0. With regard to group B, compounds are preferred where B is —COOH, an alkali metal salt or organic amine salt, or a lower alkyl ester therof.

In the preferred compounds of the invention R$_1$ and R$_3$ are H or lower alkyl of 1 to 6 carbons, most preferably these groups are methyl. The R$_2$, R$_4$ and R$_5$ groups are preferably H or lower alkyl of 1 to 6 carbons, most preferably H. The most preferred compounds of the invention are shown in Table 1 with reference to Formula 5.

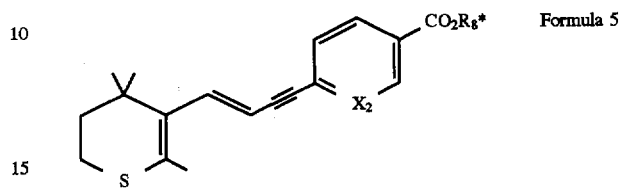

Formula 5

TABLE 1

| Compound No. | X$_2$ | R*$_8$ |
|---|---|---|
| 1 | CH | Et |
| 2 | CH | H |
| 3 | N | Et |
| 4 | N | H |

MODES OF ADMINISTRATION

The compounds of this invention may be administered systemically or topically, depending on such considerations as the condition to be treated, need for site-specific treatment, quantity of drug to be administered, and numerous other considerations.

In the treatment of dermatoses, it will generally be preferred to administer the drug topically, though in certain cases such as treatment of severe cystic acne or psoriasis, oral administration may also be used. Any common topical formulation such as a solution, suspension, gel, ointment, or salve and the like may be used. Preparation of such topical formulations are well described in the art of pharmaceutical formulations as exemplified, for example, Remington's Pharmaceutical Science, Edition 17, Mack Publishing Company, Easton, Pa. For topical application, these compounds could also be administered as a powder or spray, particularly in aerosol form. If the drug is to be administered systemically, it may be confected as a powder, pill, tablet or the like or as a syrup or elixir suitable for oral administration. For intravenous or intraperitoneal administration, the compound will be prepared as a solution or suspension capable of being administered by injection. In certain cases, it may be useful to formulate these compounds by injection. In certain cases, it may be useful to formulate these compounds in suppository form or as extended release formulation for deposit under the skin or intramuscular injection.

Other medicaments can be added to such topical formulation for such secondary purposes as treating skin dryness; providing protection against light; other medications for treating dermatoses; medicaments for preventing infection, reducing irritation, inflammation and the like.

Treatment of dermatoses or any other indications known or discovered to be susceptible to treatment by retinoic acid-like compounds will be effected by administration of the therapeutically effective dose of one or more compounds of the instant invention. A therapeutic concentration will be that concentration which effects reduction of the particular condition, or retards its expansion. In certain instances, the compound potentially may be used in prophylactic manner to prevent onset of a particular condition.

A useful therapeutic or prophylactic concentration will vary from condition to condition and in certain instances may vary with the severity of the condition being treated and the patient's susceptibility to treatment. Accordingly, no single concentration will be uniformly useful, but will require modification depending on the particularities of the disease being treated. Such concentrations can be arrived at through routine experimentation. However, it is anticipated that in the treatment of, for example, ache, or similar dermatoses, that a formulation containing between 0.01 and 1.0 milligrams per mililiter of formulation will constitute a therapeutically effective concentration for topical application. If administered systemically, an amount between 0.01 and 5 mg per kg per day of body weight would be expected to effect a therapeutic result in the treatment of many disease for which these compounds are useful.

ASSAY OF RETINOID-LIKE BIOLOGICAL ACTIVITY

The retinoid-like activity of these compounds is confirmed through the classic measure of retinoic acid activity involving the effects of retinoic acid on ornithine decarboxylase. The original work on the correlation between retinoic acid and decrease in cell proliferation was done by Verma & Boutwell, Cancer Research, 1977, 37,2196–2201. That reference discloses that ornithine decarboxylase (ODC) activity increased precedent to polyamine biosynthesis. It has been established elsewhere that increases in polyamine synthesis can be correlated or associated with cellular proliferation. Thus, if ODC activity could be inhibited, cell hyperproliferation could be modulated. Although all causes for ODC activity increases are unknown, it is known that 12-0-tetradecanoylphorbol-13-acetate (TPA) induces ODC activity. Retinoic acid inhibits this induction of ODC activity by TPA. An assay essentially following the procedure set out in Cancer Res: 1662–1670,1975 may be used to demonstrate inhibition of TPA induction of ODC by compounds of this invention. The results of this assay for certain exemplary compounds of the invention are shown in Table 1 below, wherein either the $IC_{80}$ or $IC_{60}$ value for each exemplary compound is indicated in namolar concentration units. (As is known in the art, the $IC_{60}$ value is that concentration of the compound (in nanomols) which results in 60% inhibition.)

TABLE 1

| Compound # | $IC_{60}$ | $IC_{80}$ |
|---|---|---|
| 1 | 3.8 | — |
| 2 | 1.4 | — |
| 3 | — | 28 |
| 4 | — | 33.6 |

SPECIFIC EMBODIMENTS

Synthetic Processes for Preparing Compounds of the Invention

The compounds of this invention can be made by a number of different synthetic chemical pathways. To illustrate this invention, there is here outlined a series of steps which have been proven to provide the compounds of Formula 1 when such synthesis is followed in fact and in spirit. The synthetic chemist will readily appreciate that the conditions set out here are specific embodiments which can be generalized to any and all of the compounds represented by Formula 1. Furthermore, the synthetic chemist will readily appreciate that the herein described synthetic steps may be varied and or adjusted by those skilled in the art without departing from the scope and spirit of the invention.

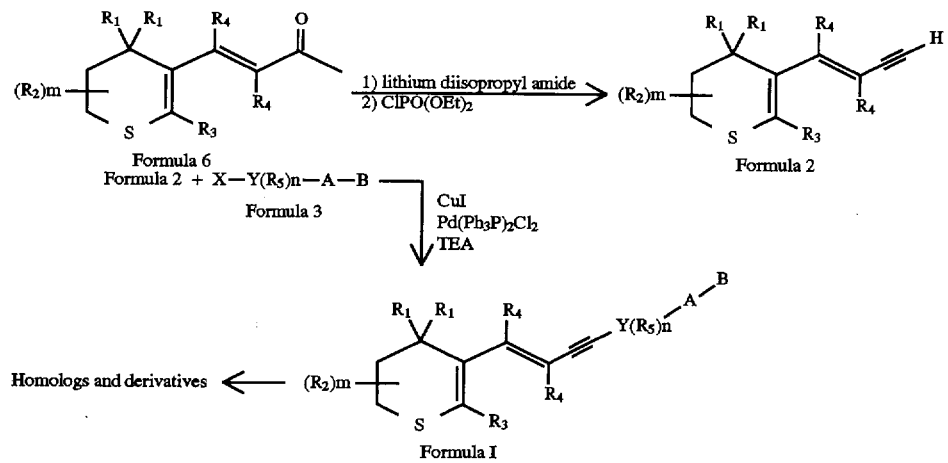

Reaction Scheme 1

Referring now to Reaction Scheme 1 a (3'-thioxacyclohexyl-enyl)-but-1-ene-3-one derivative of Formula 6 which has the desired $R_1$, $R_2$, $R_3$ and $R_4$ substituents is reacted with with strong base, such as lithium diisopropyl amide, and diethyl chlorophosphate, to introduce the triple bond into the molecule and yield the (3'-thioxacyclohexyl-enyl)-but-1-ene-3-yne derivative of Formula 2. The starting material, compound of Formula 6, can be obtained in accordance with the state of the art. An example for a compound of Formula 6, which is used to prepare the herein described preferred examples of the compounds of the invention is 1-(2',4',4'-trimethyl-1'-thiacyclohex-2'-ene-3'-yl)-but-1-ene-3-one (Compound 5). Compound 5 is available in accordance with chemical literature, as described in Tetrahedron 1966, 22 pp259–264. Thus, in accordance with the first step shown in Reaction Scheme 1, Compound 5 is converted into 1-(2',4',4'-trimethyl-1'-thiacyclohex-2'-ene-3'-yl)-but-1-ene-3-yne (Compound 6).

In order to introduce a phenyl or heteroaryl substitutent on the acetylene (ethyne) portion of a compound of Formula 2, the latter compound is coupled with the reagent X—Y(R$_5$)n—A—B (Formula 3). In other words, the phenyl or heteroaryl substitutent is introduced into the (3'-thioxacyclohexyl-enyl)]-but-1-ene-3-yne derivative of Formula 2 by reacting the latter with a halogen substituted phenyl or heteroaromatic compound of Formula 3 in which the phenyl or heteroaromatic nucleus (Y) either has the desired substituent (A—B) or wherein the actual subsituent A—B can be readily converted to the desired substituent by means of organic reactions well known in the art.

Coupling of the (3'-thioxacyclohexyl-enyl)]-but-1-ene-3-yne derivative of Formula 2 with the reagent X-13 Y(R$_5$)n-A-B (Formula 3) is affected directly in the presence of cuprous iodide, a suitable catalyst, typically of the formula Pd(PQ$_3$)Cl$_2$ (Q is phenyl) and an acid acceptor, such as triethylamine, in an inert gas (argon) atmosphere. Alternatively, a metal salt, such as the zinc salt of Formula 4 derived from the ethynyl compound of Formula 2 is reacted with the reagent of Formula 3 in the presence of a palladium complex catalyst having the formula Pd(PQ$_3$)$_4$ (Q is phenyl) or similar complex. Generally speaking, coupling between an ethynylbenzene compound or its zinc salt and a halogen substituted aryl or heteroaryl compound, such as the reagent of Formula 3, is described in U.S. Pat. No. 5,264,456, the specification of which is expressly incorporated herein by reference. Coupling between 1-(2',6',6'-trimethylcyclohex-1'-enyl)but-1-ene-3-yne and ethyl 6-chlorinicotinate is described in U.S. Pat. No. 4,927,947, and coupling between 1-(2',6',6'-trimethylcyclohex-1'-enyl) but-1-ene-3-yne and ethyl 4-iodobenzoate is described in U.S. Pat. No. 4,739,098. The specification of U.S. Pat. No. 4,927,947 and 4,739,098 are expressly incorporated herein by reference.

The disubstituted acetylene compounds of Formula 1 which result from the coupling reaction shown in Reaction Scheme 1 may be the target compounds made in accordance with the invention, or may be readily converted into the target compounds by such steps as salt formation, esterification, deesterification, homologation, amide formation and the like. These steps are further discussed below, and are indicated in Reaction Scheme 1 as conversion into homologs and derivatives.

Carboxylic acids are typically esterified by refluxing the acid in a solution of the appropriate alcohol in the presence of an acid catalyst such as hydrogen chloride or thionyl chloride. Alternatively, the carboxylic acid can be condensed with the appropriate alcohol in the presence of dicyclohexylcarbodiimide and dimethylaminopyridine. The ester is recovered and purified by conventional means. Acetals and ketals are readily made by the method described in March, "Advanced Organic Chemistry," 2nd Edition, McGraw-Hill Book Company, p 810). Alcohols, aldehydes and ketones all may be protected by forming respectively, ethers and esters, acetals or ketals by known methods such as those described in McOmie, Plenum Publishing Press, 1973 and *Protecting Groups, Ed. Greene, John Wiley & Sons*, 1981.

A means for making compounds where A is (CH$_2$)$_n$ (n is 1–5) is to subject the compounds of Formula 1, where B is an acid or other function, to homologation, using the well known Arndt-Eistert method of homologation, or other known homologation procedures.

Compounds of Formula 1, where A is an alkenyl group having one or more double bonds can be made for example, by having the requisite number of double bonds incorporated into the reagent of Formula 3 which is reacted with the ethyne compound or its metal salt, as shown in Reaction Scheme 1. Generally speaking, such compounds where A is an unsaturated carbon chain can be obtained by synthetic schemes well known to the practicing organic chemist; for example by Wittig and like reactions, or by introduction of a double bond by elimination of halogen from an alphahalo-carboxylic acid, ester or like carboxaldehyde. Compounds of Formula 1 where the A group has a triple (acetylenic) bond can be made by using the corresponding aryl or heteroaryl aldehyde intermediate. Such intermediate can be obtained by reactions well known in the art, for example, by reaction of a corresponding methyl ketone with strong base, such as lithium diisopropyl amide.

The acids and salts derived from compounds of Formula 1 are readily obtainable from the corresponding esters. Basic saponification with an alkali metal base will provide the acid. For example, an ester of Formula 1 may be dissolved in a polar solvent such as an alkanol, preferably under an inert atmosphere at room temperature, with about a three molar excess of base, for example, potassium hydroxide, sodium hydroxide or lithium hydroxide. The solution is stirred for an extended period of time, between 15 and 20 hours, cooled, acidified and the hydrolysate recovered by conventional means. The synthesis of carboxylic acids from the esters which are obtained in the coupling step between a reagent of Formula 2 and of Formula 3 (where B represents for example COOC$_2$H$_5$) is a step that leads to several preferred compounds of the present invention.

The amide may be formed by any appropriate amidation means known in the art from the corresponding esters or carboxylic acids. One way to prepare such compounds is to convert an acid to an acid chloride and then treat that compound with ammonium hydroxide or an appropriate amine.

Alcohols are made by converting the corresponding acids to the acid chloride with thionyl chloride or other means (J. March, "Advanced Organic Chemistry", 2nd Edition, McGraw-Hill Book Company), then reducing the acid chloride with sodium borohydride (March, Ibid, pg. 1124), which gives the corresponding alcohols. Alternatively, esters may be reduced with lithium aluminum hydride at reduced temperatures. Alkylating these alcohols with appropriate alky halides under Williamson reaction conditions (March, Ibid, pg. 357) gives the corresponding ethers. These alcohols can be converted to esters by reacting them with appropriate acids in the presence of acid catalysts or dicyclohexylcarbodiimide and dimethlaminopyridine.

Aldehydes can be prepared from the corresponding primary alcohols using mild oxidizing agents such as pyridinium dichromate in methylene chloride (Corey, E. J., Schmidt, G., *Tet. Lett.*, 399, 1979), or dimethyl sulfoxide/ oxalyl chloride in methylene chloride (Omura, K., Swern, D., *Tetrahedron*, 1978, 34, 1651).

Ketones can be prepared from an appropriate aldehyde by treating the aldehyde with an alkyl Grignard reagent or similar reagent followed by oxidation.

Acetals or ketals can be prepared from the corresponding aldehyde or ketone by the method described in March, Ibid, p 810.

Compounds of Formula 1 where B is H can be prepared from the corresponding halogenated aromatic compounds, preferably where the halogen is I.

The reagent of Formula 3 is generally speaking available in accordance with the chemical literature, or when necessary can be obtained, within the skill of the practicing organic chemist, in accordance with the reaction steps outlined above. Preferred methods for the syntheses of certain reagents of Formula 3 (where A—B represents —COOR₈) which are used for the preparation of the preferred examples of the present invention, are also described below.

SPECIFIC EXAMPLES

Ethyl 4-iodobenzoate

To a suspension of 10 g (40.32 mmol) of 4-iodobenzoic acid in 100 ml absolute ethanol was added 2 ml thionyl chloride and the mixture was then heated at reflux for 3 hours. Solvent was removed in vacuo and the residue was dissolved in 100 ml ether. The ether solution was washed with saturated NaHCO₃ and saturated NaCl solutions and dried (MgSO₄). Solvent was then removed in vacuo and the residue kugelrohr distilled (100 degrees C.; 0.55 mm) to give the title compound as a colorless oil, PMR (CDCl₃): 1.42 (3H, t, J~7 Hz), 4,4 (2H, q, J~7 Hz), 7.8 (4H).

6-Iodonicotinic acid

To 27.97 g (186.6 mmol) of sodium iodide cooled to −78° C. was added 121.77 g (71.6 ml, 952.0 mmol) of hydriodic acid (in 57 wt % aqueous solution). The reaction mixture was allowed to warm slightly with stirring for 5 minutes, and then 30.00 g (190.4 mmol) of 6-chloronicotinic acid was added. The resulting mixture was allowed to warm to room temperature with stirring and then heated at 120°–125° C. in an oil bath for 42 hours. A dark brown layer formed above the yellow solid material. The reaction mixture was allowed to cool to room temperature and then poured into acetone (chilled to 0° C.). The resultant yellow solid was collected by filtration, washed with 200 ml of 1N NaHSO₃ solution, and dried in vacuum (3 mm Hg) to give the title compound as a pale yellow solid.
PMR (DMSO-d₆): d 7.90 (1H, dd, J=8.1, 2 Hz), 7.99 (1H, d, J=8.1 Hz), 8.80 (1H, d, J=2 Hz).

Ethyl 6-iodonicotinoate

To a suspension of 23.38 g (94.2 mmol) of 6-iodonicotinic acid in 100 ml of dichloromethane was added a solution of 19.86 g (103.6 mmol) of 1-(3-dimethylaminopropyl)-3-ethylcarbodiimide hydrochloride in 250 ml of dichloromethane. To this suspension was added 12.40 g (15.8 ml, 269.3 mmol) of ethanol (95%) and 1.15 g (9.4 mmol) of 4-dimethylaminopyridine. The resulting solution was then heated at 50° C. in an oil bath for 24.5 hours, concentrated in vacuo, partitioned between 200 ml of water and 250 ml of ethyl ether, and the layers were separated. The aqueous phase was washed with 2×150 ml-portions of ethyl ether. All organic phases were combined, washed once with 75 ml of brine solution, dried over MgSO₄, filtered and concentrated in vacuo to yield a yellow solid residue. Purification by flash chromatography (silica, 10% ethyl acetate in hexane) yielded the title compound as a white solid.
PMR (CDCl₃): d 1.41 (3H, t, J=7.1 Hz), 4.41 (2H, q, J=7.1 Hz), 7.85 (1H, d, J=8.2 Hz), 7.91 (1H, dd, J=8.2, 2.1 Hz), 8.94 (1H, d, J=2.1 Hz).

1-(2',4',4'-Trimethyl-1'-thiacyclohex-2'-ene-3'-yl)-but-1(E)-ene-3-yne (Compound 6)

To a solution of lithium diisopropyl amide (LDA) prepared at 0° C. by mixing diisopropylamine (0.06 ml) and BuLi (1.7M in hexane, 0.26 ml) in 3 ml of THF was added dropwise 1-(2',4',4'-trimethyl-1'-thiacyclohex-2'-ene-3'-yl)-but-1-ene-3-one (Compound 5, 4-thiaionone, 84 mg, 0.4 mmol) at −78° C. (Compound 5 is available in accordance with *Tetrahedron* 1966, 22 pp259–264, incorporated herein by reference.) The reaction mixture was stirred for 1 hour when diethyl chlorophosphate (0.06 ml) was added at −78° C. The reaction mixture was gradually warmed to room temperature and then transferred through cannulation into a solution of LDA at −78° C., prepared as above. The reaction mixture was slowly warmed to room temperature and left overnight. Water was added to the reaction mixture and the mixture was extracted into ethyl acetate. The organic layer was washed with 10% of HCl, NaHCO₃, brine and dried over MgSO₄. The solvent was evaporated and the residue was purified by column chromatography (ethyl acetate/hexane 1/10) to give the title compound as a yellow oil (50 mg).
¹H NMR δ (CDCl₃) 6.66 (d, J=16.5 Hz, 1H), 5.43 (dd, J=16.3, 2.3 Hz, 1H), 2.96 (d, J=2.3 Hz, 1H), 2.83 (m, 2H), 1.95 (s, 3H), 1.85 (m, 2H), 1.09 (s, 6H).

Ethyl 4-[4'-(2",6",6",-Trimethyl-3"-thioxacyclohex-1"-enyl)-but-3'(E)-ene-1'-ynyl]benzoate (Compound 1)

A solution of 1-(2',4',4'-trimethyl-1'-thiacyclohex-2'-ene-3'-yl)-but-1-ene-3-yne (Compound 6, 232 mg, 1.21 mmol), CuI (45.9 mg) and ethyl 4-iodobenzoate (334 mg, 1.21 mmol) in 10 ml of triethylamine (TEA) was purged with N₂ for 1 minute before Pd(Ph₃P)₂Cl₂ (255 mg) was added to the solution. The resulting yellow slurry was stirred at room temperature for 2 days. The reaction was filtered and the solution was concentrated to give a brown residue. The residue was purified by column chromatography (ethyl acetate/hexane 1/50) to give the title compound as a yellow oil (248 mg, 60%).
¹H NMR δ (CDCl₃) 7.99 (d, J=8.5 Hz, 2H), 7.49 (d, J=8.5 Hz, 2H), 6.72 (d, J=15.6 Hz, 1H), 5.68 (d, J=15.6 Hz, 1H), 4.37 (q, J=7.1 Hz, 2H), 2.85 (m, 2H), 2.00 (s, 3H), 1.86 (m, 2H), 1.40 (t, J=7.2 Hz, 3H), 1.12 ( s, 6H) .

4-[4'-(2",6",6"-Trimethyl-3"-thioxacyclohex-1"-enyl) -but-3'(E)-ene-1'-ynyl]benzoic Acid (Compound 2)

To a solution of ethyl 4-[4'-(2",6",6"-trimethyl-3"-thioxacyclohex-1"-enyl )-but-3'-ene-1'-ynyl]benzoate (Compound 1, 130 mg) in 3 ml of EtOH was added 1 ml of 1N NaOH. The reaction mixture was stirred at room temperature for 12 hours. The solvent was removed and ethyl acetate was added to the residue. The resulting solution was washed with 10% of HCl until the aqueous layer became neutral. The organic layer was separated, washed with brine and dried over MgSO₄. After concentration, the residue was purified by column chromatography (ethyl acetate/hexane 1/1) to give the title compound as a yellow crystals (95 mg).
¹H NMR δ (CDCl₃) 8.03 (d, J=8.3 Hz, 2H), 7.52 (d, J=8.3 Hz, 2H), 6.74 (d, J=15.9 Hz, 1H), 5.69 (d, J=15.9 Hz, 1H), 2.86 (m, 2H), 2.01 (s, 3H), 1.86 (m, 2H), 1.14 (s, 6H).

Ethyl 6-[4'-(2",6",6"-Trimethyl-3"-thioxacyclohex-1"-enyl)-but-3'(E)-ene-1'-ynyl]nicotinate (Compound 3)

Using the same procedure as for the synthesis of ethyl 4-[4'-(2",6",6",-trimethyl-3"-thioxacyclohex-1"-enyl)-but-3'-ene-1'-ynyl]benzoate (Compound 1) but using 50 mg of 1-(2',4',4'-trimethyl-1'-thiacyclohex-2'-ene-3'-yl)-but-1-ene-3-yne (Compound 5), 72 mg of ethyl 6-iodo nicotinate, 55 mg of Pd(Ph₃P)₂Cl₂ and 9.9 mg of CuI in 2 ml of TEA, the title compound was obtained as a yellow oil (59 mg, 67%).
1H NMR δ (CDCl₃) 9.08 (d, J=2.1 Hz, 1H), 8.27 (dd, J=8.2, 2.2 Hz, 1H), 7.60 (d, J=9.28 Hz, 1H), 6.90 (d, J=16.5 Hz, 1H), 5.80 (d, J=16.4 Hz, 1H), 4.37 (q, J=7.1 Hz, 2H), 2.88 (m, 2H), 1.98 (s, 3H), 1.87 (m, 2H), 1.37 (t, J=7.1 Hz, 3H), 1.15 (s, 6H).

6-[4'-(2",6",6"-Trimethyl-3"-thioxacyclohex-1"-enyl)-but-3'(E)-ene-1'-ynyl]nicotinic Acid (Compound 4)

Using the same procedure as for the synthesis of 4-[4'-(2",6",6"-trimethyl-3"-thioxacyclohex-1"-enyl)-but-3'-ene-1'-ynyl]benzoic acid (Compound 2) but using ethyl 6-[4'-(2",6",6",-trimethyl-3"-thioxacyclohex-1"-enyl)-but-3'-ene-1'-ynyl]nicotinate ( Compound 3, 15 mg), the title compound was obtained as a yellow solid (12 mg, 80%).
$^1$H NMR δ (CDCl$_3$) 9.29 (s, 1H), 8.34 Hz (d, J=8.3 Hz, 1H), 7.53 (d, J=8.2 Hz, 1H), 6.91 (d, J=16.1 Hz, 1H), 5.74 (d, J=16.1 Hz, 1H), 2.86 (m, 2H), 2.01 (s, 3H), 1.86 (m, 2H), 1.14 (s, 6H).

What is claimed is:

1. A compound of the formula

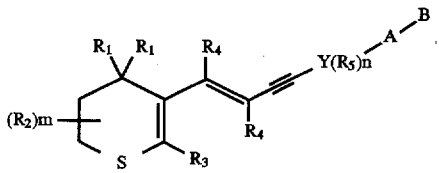

where $R_1$, $R_2$, $R_3$, and $R_4$ independently are H or lower alkyl of 1 to 10 carbons;

$R_5$ is lower alkyl of 1 to 10 carbons, fluoro, chloro, bromo, iodo, nitro, or fluoroalkyl having 1 to 10 carbons;

m is an integer having the value of 1–4;

n is an integer having the value of 0–4;

Y is phenyl or a heteroaryl group selected from a group consisting of pyridyl, thienyl, furyl, pyridazinyl, pyrimidinyl, pyrazinyl, thiazolyl and oxazolyl, said Y group being optionally substituted with one or more $R_5$ group;

A is $(CH_2)_p$ where p is 0–5, lower branched chain alkyl having 3–6 carbons, cycloalkyl having 3–6 carbons, alkenyl having 2–6 carbons and 1 or 2 double bonds, alkynyl having 2–6 carbons and 1 or 2 triple bonds, and B is hydrogen, COOH or a pharmaceutically acceptable salt thereof, COOR$_8$, CONR$_9$R$_{10}$, —CH$_2$OH, CH$_2$OR$_{11}$, CH$_2$OCOR$_{11}$, CHO, CH(OR$_{12}$)$_2$, CHOR$_{13}$O, —COR$_7$, CR$_7$(OR$_{12}$)$_2$, or CR$_7$OR$_{13}$O, where R$_7$ is an alkyl, cycloalkyl or alkenyl group containing 1 to 5 carbons, R$_8$ is an alkyl group of 1 to 10 carbons, or a cycloalkyl group of 5 to 10 carbons, or R$_8$ is phenyl or lower alkylphenyl, R$_9$ and R10 independently are hydrogen, an alkyl group of 1 to 10 carbons, or a cycloalkyl group of 5–10 carbons, or phenyl or lower alkylphenyl, R$_{11}$ is lower alkyl, phenyl or lower alkylphenyl, R$_{12}$ is lower alkyl, and R$_{13}$ is divalent alkyl radical of 2–5 carbons.

2. A compound in accordance with claim 1 where Y is selected from a group consisting of phenyl, pyridyl, thienyl and furyl.

3. A compound in accordance with claim 2 where Y is phenyl.

4. A compound in accordance with claim 3 where the phenyl group is 1,4 substituted by the ethynyl and A—B groups.

5. A compound in accordance with claim 4 where A is $(CH_2)_p$, p is 0 and and B is COOH, COOR$_8$ or CONR$_9$R$_{10}$.

6. A compound in accordance with claim 2 where Y is pyridyl.

7. A compound in accordance with claim 6 where the pyridyl group is 2,5 substituted by the ethynyl and A—B groups.

8. A compound in accordance with claim 7 where A is $(CH_2)_n$, n is 0 and and B is COOH, COOR$_8$ or CONR$_9$R$_{10}$.

9. A compound of the formula

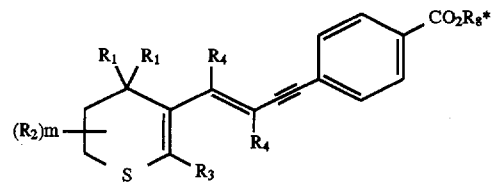

where $R_1$, $R_2$, $R_3$, and $R_4$ independently are H or lower alkyl of 1 to 10 carbons;

m is an integer having the value of 1–4, and $R_8$* is H, an alkyl group of 1 to 10 carbons or a pharmaceutically acceptable cation.

10. A compound an accordance with claim 9 where R$_4$ is H or CH$_3$.

11. A compound an accordance with claim 9 where R$_3$ is H or CH$_3$.

12. A compound in accordance with claim 9 where R$_1$ is H or CH$_3$.

13. A compound an accordance with claim 9 where R$_1$ is CH$_3$, m is 0, R$_3$ is CH$_3$, and R$_4$ is H.

14. A compound an accordance with claim 13 where R$_8$* is H, or a pharmaceutically acceptable cation.

15. A compound in accordance with claim 13 where R$_8$* is CH$_3$CH$_2$.

16. A compound of the formula

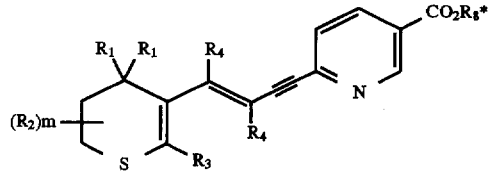

where $R_1$, $R_2$, $R_3$, and $R_4$ independently are H or lower alkyl of 1 to 10 carbons;

m is an integer having the value of 1–4, and $R_8$* is H, an alkyl group of 1 to 10 carbons or a pharmaceutically acceptable cation.

17. A compound in accordance with claim 16 where R$_4$ is H or CH$_3$.

18. A compound in accordance with claim 16 where R$_3$ is H or CH$_3$.

19. A compound in accordance with claim 16 where R$_1$ is H or CH$_3$.

20. A compound in accordance with claim 16 where R$_1$ is CH$_3$, m is 0, R$_3$ is CH$_3$, and R$_4$ is H.

21. A compound in accordance with claim 20 where R$_8$* is H or a pharmaceutically acceptable cation.

22. A compound in accordance with claim 20 where R$_8$* is CH$_3$CH$_2$.

* * * * *

UNITED STATES PATENT AND TRADEMARK OFFICE
CERTIFICATE OF CORRECTION

PATENT NO. : 5,688,957
DATED : November 18, 1997
INVENTOR(S) : Teng et al.

It is certified that error appears in the above-identified patent and that said Letters Patent is hereby corrected as shown below:

Column 1, line 14, "thioxacyclohexyl"-enyl" should be --thioxacyclohex-1"-enyl--.

Column 2, line 16, both occurrence of "4,4-disubsituted" should be --4,4-disubstituted--.

Column 2, line 17, "4,4-disubsituted" should be --4,4-disubstituted--.

Column 2, line 43, "epoxycyclohaxanyl" should be --epoxycyclohexanyl--.

Column 4, line 19, "Pd(PQ$_3$)2Cl$_2$" should be --Pd(PQ$_3$)$_2$Cl$_2$--.

Column 6, line 61, "effected" should be --affected--.

Column 6, line 64, "effects" should be --affects--.

Column 8, line 51, please delete the second occurrence of "with".

Column 9, line 3, "substitutent" should be --substituent--.

Colunm 10, line 46, "dimethlaminopyridine" should be --dimethylaminopyridine--.

Column 13, line 66, please delete the second occurrence of "and".

Column 14, line 7, please delete the second occurrence of "and".

UNITED STATES PATENT AND TRADEMARK OFFICE
CERTIFICATE OF CORRECTION

PATENT NO. : 5,688,957
DATED : November 18, 1997
INVENTOR(S) : Teng et al.

It is certified that error appears in the above-identified patent and that said Letters Patent is hereby corrected as shown below:

Page 2, under References Cited, first column, patent no. "5,005,550" should be --5,006,550--.

Column 7, line 9, "ache" should be --acne--.

Column 9, line 12, after "X-", delete "13".

Column 13, line 13, after the no. "8.34", delete "Hz".

Column 13, line 51, "R10" should be --$R_{10}$--.

Column 14, line 24, "an" should be --in--.

Column 14, line 26, "an" should be --in--.

Column 14, line 30, "an" should be --in--.

Column 14, line 32, "an" should be --in--.

Signed and Sealed this

Twenty-ninth Day of August, 2000

Attest:

Q. TODD DICKINSON

*Attesting Officer*  *Director of Patents and Trademarks*